United States Patent
Krakovitz

(10) Patent No.: US 6,212,423 B1
(45) Date of Patent: Apr. 3, 2001

(54) DIAGNOSTIC HYBRID PROBES

(76) Inventor: Mark Krakovitz, 315 Myrtle La., Narberth, PA (US) 19072

( * ) Notice: Subject to any disclaimer, the term of this patent is extended or adjusted under 35 U.S.C. 154(b) by 0 days.

(21) Appl. No.: 09/211,479

(22) Filed: Dec. 14, 1998

Related U.S. Application Data

(63) Continuation-in-part of application No. 08/717,134, filed on Sep. 20, 1996, which is a continuation of application No. 08/550,516, filed on Oct. 20, 1995, now abandoned, which is a continuation of application No. 08/204,581, filed on Mar. 2, 1994, now abandoned.

(51) Int. Cl.⁷ ........................................................ A61B 6/00
(52) U.S. Cl. ...................................... 600/473; 250/370.11
(58) Field of Search ..................................... 600/436, 437; 250/358.1, 363.01, 336.1, 370.11; 424/9.1

(56) References Cited

U.S. PATENT DOCUMENTS

| 4,995,396 | 2/1991 | Inaba et al. | 600/436 |
| 5,014,708 | 5/1991 | Hayashi et al. | 600/436 |
| 5,846,513 | 12/1998 | Carroll et al. | 424/111 |

*Primary Examiner*—Brian L. Casler
(74) *Attorney, Agent, or Firm*—Obermayer Rebmann Maxwell & Hippel LLP

(57) ABSTRACT

This invention is directed to a novel hybrid nuclear and ultrasonic probe comprising a cylindrical outer casing surrounding a nuclear probe comprising two scintillator plates intersecting perpendicularly, each of the scintillator plates having a plurality of parallel collimators; and an ultrasonic probe situated between said casing at the intersection of said scintillator plates.

13 Claims, 5 Drawing Sheets

DIAGNOSTIC HYBRID PROBES

CLAIM OF PRIORITY

This application is a continuation-in-part of co-pending U.S. Ser. No. 08/717,134, filed Sep. 20, 1996, which is a continuation of U.S. Ser. No. 08/550,516 which was filed on Oct. 20, 1995, now abandoned which is a continuation of U.S. Ser. No. 08/204,581 filed Mar. 2, 1994 now abandoned.

FIELD OF THE INVENTION

This invention relates to the detection of diseases. More specifically, this invention relates to a novel apparatus for the detection of diseases using both ultrasonic and nuclear energy.

BACKGROUND OF THE INVENTION

Devices for examining potentially diseased areas of the body have been used for many years for diagnostic purposes. Magnetic resonance imaging (MRI) machines, ultrasound devices, CAT scanners and X-ray imagers are but a few of the commonly utilized tools that medical radiologists have at their disposal to characterize and understand many of the maladies that afflict patients.

Well-known ultrasound devices use acoustical energy to characterize areas in the body for many different reasons. Particularly useful for displaying fluid flow, acoustical energy detected by ultrasound probes can be used in diverse applications, for example, to examine blood flow in and around diseased tissue, or to investigate the health of a fetus growing in the womb. Since ultrasound devices use acoustical energy to perform their function, they are "active" devices which first emit energy, and then detect reflected energy which has been partially absorbed.

Recently, the development of nuclear probes has given physicians yet another modality to explore and diagnose disease. Nuclear probes are unique and sophisticated devices that take advantage of the fact that diseased tissue tends to absorb substances that emit radiation. Thus, radiopharmaceuticals or radiolabeled monoclonal antibodies (MaB) that emits gamma radiation can be used to label diseased tissues which can then be examined with a nuclear probe.

Generally, the labeled tissue accumulates a higher concentration of the gamma-emitting substance so that the tissue appears "hot" to the probe, that is, more gamma radiation is emitted from the diseased tissue than from other surrounding areas. Since it is known that diseased tissue will more readily absorb the radiopharmaceutical or radiolabeled MaB, the probe thus locates the diseased tissue by detecting the hot area.

A typical nuclear probe that performs along the lines mentioned above is the Radiation Monitoring Devices, Inc. (Watertown, Mass.) Nuclear Surgical Probe System. Primarily for use in surgical applications, the Nuclear Surgical Probe System comprises a solid state Cadmium Telluride (CdTe) detector that detects gamma radiation from about 12 keV to about 1 MeV, a high gain field effect transistor preamplifier, and a counting subsystem with a display which performs diagnostic analysis and which can be interfaced to a personal computer.

Nuclear probes are reliable and innovative devices for locating diseased areas. However, these devices cannot further evaluate the diseased tissue in relation to the patient's anatomy after the tissue has been located. The radiological imaging art has therefore lacked an efficient tool which can both pinpoint the presence of the diseased tissue, characterize the diseased tissue and see its relationship to normal anatomic structures to develop a course of medical and/or surgical treatment.

There has therefore been a failure in the art to develop versatile clinical tools for disease detection and diagnosis. This has resulted in an inability to effectively treat potentially life-threatening diseases at early stages. Early disease detection allows for more effective treatment, significantly improving a patient's prognosis. This ability would not only save lives but contribute to the reduced cost of health care.

SUMMARY OF THE INVENTION

The present invention is directed to a hybrid probe comprising a substantially cylindrical probe for locating and characterizing disease comprising a scintillator having parallel collimators for examining a potentially diseased area as a function of electromagnetic radiation emitted from the area, an ultrasonic sensor situated on said scintillator for examining the potentially diseased area with ultrasonic energy, wherein the scintillator and ultrasonic sensor are adapted to characterize the potentially diseased area interactively, and processing means interfaced to at least the first means for analyzing data collected by at least one of the first or second means and for analyzing the data to characterize the disease in the potentially diseased area.

In a further embodiment, the present invention further comprises a novel hybrid probe comprising a cylindrical outer casing surrounding a nuclear probe, said nuclear probe comprising a scintillator extending axially the length of the casing, said scintillator having a plurality of parallel collimators extending therefrom, and an ultrasonic probe affixed within the casing on said scintillator and extending the length of the scintillator.

In a further embodiment to the present invention, the scintillator comprises two scintillator plates intersecting substantially perpendicularly, and the ultrasonic probe is situated at the intersection of the scintillator plates and extends their lengths. In a further embodiment of the present invention, the scintillator is curved. In still a further embodiment of the present invention, the scintillator is flat.

The hybrid probe of the present invention defines a new modality with unique characteristics and capabilities that produce increased benefits in the detection and diagnosis of diseases. The hybrid probe is designed to detect and diagnose disease using a dual mode, combining ultrasound and nuclear medicine to produce images with specificity that is unattainable with existing and even proposed imaging methods.

The hybrid probe of the present invention defines a new "interactive" method and increased versatility for application to the detection and diagnosis of numerous diseases. It is the only imaging modality that combines the unique characteristics of ultrasound and nuclear medicine in the manner described, delivered in a non-invasive, easily portable device for the advanced detection and diagnostic results.

This invention allows ultrasound and nuclear medicine images to be obtained simultaneously in real-time three dimension, enables complete integration of ultrasound and nuclear medicine images simultaneously with 3D perspective including, X, Y, Z coordinates of a tumor or other significant disease and with wide field of view to see relationship to normal structures. The images produced will be a hybrid anatomical (ultrasound) and functional (nuclear medicine) image which renders, in one exam, much greater information than each individual exam could produce. The results are images that combine the best qualities of each modality to provide new diagnostic information that is unobtainable with existing or proposed imaging methods and/or devices.

Hybrid probes provided in accordance with the present invention will provide superior diagnostic capabilities than individual ultrasound or nuclear probes which have heretofore been known and used in the art. Greater sensitivity and specificity of disease detection and characterization will be accomplished with such hybrid probes, and therefore early detection of diseases will be accomplished. This will inevitably result in saving lives and reducing the cost of health care. Such results have not heretofore been achieved in the art.

DETAILED DESCRIPTION OF PREFERRED EMBODIMENTS

Figure 1:
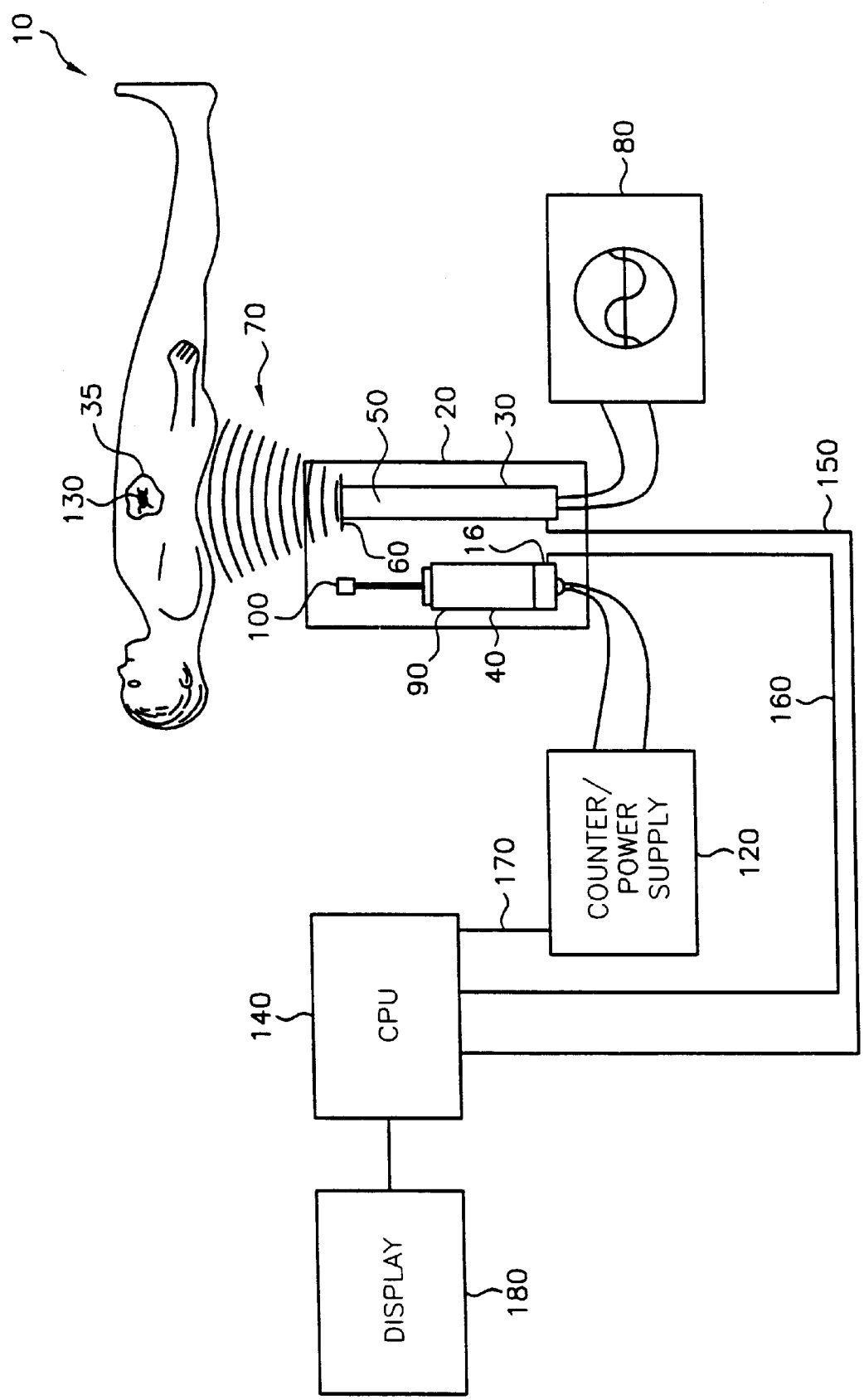
FIG. 1 is a schematic representation of a system for diagnosing disease provided in accordance with the present invention which comprises a nuclear probe and an ultrasound device.

Referring now to the Figures, in FIG. 1 a patient 10 undergoes examination with a combined or hybrid probe shown generally at 20. The patient could be undergoing examination with probe 20 prior to a surgical or therapeutic technique, or could be examined by probe 20 during surgery or as part of the patient's therapy. For exemplary purposes, the patient is shown with a potentially diseased area 35 that is involved with a cancer or other disease which is potentially life-threatening. Through use of the hybrid probe 20, a system is provided for diagnosing and characterizing disease efficiently and at an early stage.

In a preferred embodiment, hybrid probe 20 comprises an ultrasound probe shown at 30 and a nuclear probe shown at 40. Ultrasound probes are known to those with skill in the art. They generally consist of a probe body 50, and an excitation head 60 which emits acoustical or ultrasonic energy shown generally at 70 which is used to examine the potentially diseased area 35. The ultrasonic probe 30 is excited by a power supply 80 which impresses a sinusoidally varying electrical signal on probe 30 to cause head 60 to stimulate the output of the acoustical energy 70.

When the acoustical energy interacts with potentially diseased area 35, the diseased area 35 reflects back a portion of this energy and so the potentially diseased area can be characterized. Ultrasound probes of this nature are described fully in the patent literature, and particularly in U.S. Pat. No. 5,211,169, Freeland, the teachings of which are specifically incorporated herein by reference.

The nuclear probe 40 preferably comprises a probe body 90 which contains a NaI or CdTe detector shown generally at 100 and a detector pre-amplifier 110. The nuclear probe 40 is preferably sensitive to gamma radiation at energies between about 12 keV and about 1 MeV. The probe body 90 is further preferably interfaced to a counter and power supply 120. The power supply and counting system 120 is preferably powered by a rechargeable nickel cadmium battery. Counter and power supply 120 further comprises a pre-amplifier power supply, a detector biased control, a signal amplifier, a counter-time with nine counting periods and a continuous count setting, upper and lower user settable energy discriminator levels, a single channel analyzer, a six-digit LCD display, and outputs for standard recorders, rate meters or personal computers.

The CdTe detector's bias is preferably adjustable by the counter and power supply 120 in a range of about 0 to 30 volts and at settings of 45 volts and 60 volts. The nine counting periods can be set from between about 1 to about 500 seconds. A continuous count mode is also provided by the counter and power supply 120. The energy window of the counter is between about 0 to about 200 keV, or about 0 to about 1 MeV. The energy window is preferably adjustable for both upper and lower energy ranges. The pre-amplifier in the power supply 120 operates on negative pulses of about 1.5 mV per keV. The amplifier itself in the counter and power supply 120 operates on positive pulses and has gain settings of 3 or 5 mV per keV.

In order to begin the diagnosis and characterization procedure provided in accordance with the invention, patient 10 first usually is injected with a radiolabeled pharmaceutical or radiolabeled MaB. Nuclear probe 40 is particularly sensitive to the radiolabeled pharmaceuticals or MaB that will emit gamma radiation up to 140 keV, that is, the technetium-99m energy level. After the patient is injected with the radiolabeled compound, this material tends to pool or accumulate in a higher concentration in potentially diseased area 35. Potentially diseased area 35 then emits a "hot spot", shown generally at 130, which is the gamma radiation that can be detected at the CdTe solid state detector 100 of probe 40. This initially locates the diseased area, a task which ultrasound probe 30 is usually unable to accomplish by itself. After nuclear probe 40 locates and makes an initial characterization of potentially diseased area 35 and surrounding structures, ultrasound probe 30 is utilized to fully evaluate the potentially diseased area 35. Many different kinds of diseases can be evaluated, diagnosed and characterized in this manner. For example, radiolabeled MaB have been used in evaluating ovarian and colon malignancies and prostate. Thus, identification of primary ovarian malignancy can be accomplished by injecting a radiolabeled MaB and then performing transvaginal ultrasound studies using the hybrid probe 20. This leads to more accurate characterization of ovarian masses with greater sensitivity and specificity for ovarian tumors as compared to present day ultrasound or CAT scanning/MRI devices. Furthermore, staging of ovarian malignancies will be more accurate using a hybrid probe 20 such as that shown in FIG. 1.

Similarly, identification of primary colon neoplasm by using hybrid probe 20 after administration of radiolabeled MaB will show marked improvements over routine colonoscopy or barium enema examinations. It is envisioned that when radiolabeled MaB are developed for breast cancers or other cancers, a hybrid probe 20 in accordance with the present invention could also be used for superior identification and characterization of these diseases.

Hybrid probes in accordance with the present invention could also be used in conjunction with laproscopic and colonoscopic instruments to better stage ovarian and colon malignancies. Furthermore in the past, intraoperative ultrasound devices and nuclear probes have been used individually to stage other diseases, for example, tumor metastasis to the liver. With probes provided in accordance with the present invention that comprise both ultrasound and nuclear probes to locate and characterize diseases interactively, the sensitivity and specificity of probes will be improved as compared to individual ultrasound and nuclear probes. Therefore, by interactively using ultrasound probe 30 and nuclear probe 40 in a modality wherein disease is first located and then fully characterized, the physician will be provided with a superior tool for early stage diagnosis and treatment of diseases.

The technetium 99m radioisotope has been used for blood clot detection in the lungs, heart and extremities. Recently Acutect™, a functional imaging agent which incorporates technetium 99m radioisotope from Diatide, Inc. has been made commercially available. This is the only effective nuclear agent to target acute venous thrombosis in the lower extremities above and below the knee. Ultrasound itself is unreliable for differentiating chronic v. acute blood clots in the legs, a very important clinical issue. Using the combination of Acutect™ with the hybrid probe more accurate assessment of venous thrombosis in the lower extremities or elsewhere within the body could most certainly be achieved. Such a combination would take advantage of the functional imaging agent and functional nuclear imaging component of the hybrid probe and the high resolution anatomic imaging capability of the ultrasound component of the probe.

The hybrid probe will also be fully adaptable to cardiac imaging. However, as is typical with many radioisotope MaB, they experience a poor target-to-background ratio signal strength. This problem will also be obviated with a hybrid probe 20 provided in accordance with the present invention since, for example, in the case of a lower extremity or heart, the technetium-99m agent could be injected such that the hybrid probe 20 could be used to first locate the clot with nuclear probe 40 and then fully characterize the clot using ultrasound. Such a technique will be fully adaptable to cardiac imaging also. In instances of, for example, "stunned myocardium" which cannot be detected with present day imaging modalities, the hybrid probe 20 would markedly increase sensitivity and specificity in evaluating this type of heart abnormality. Cardiac ejection fractions (both right and left ventricles) as well as cardiac wall motion could be studied with the hybrid probe.

Hybrid probe 20 could also be used in a very similar manner to a present day transesophageal ultrasound probes. In this fashion, following administration of a I123IPPA radioisotope imaging agent, the heart would be scanned with the hybrid probe 20. Anatomical structures of the heart could be quickly identified by the ultrasound probe and wall motion abnormalities noted. Any areas of abnormal activity, for example, as a result of ischemia, could then be identified by nuclear probe 40 and correlated with the ultrasound findings picked up by the ultrasound probe 30 portion of hybrid probe 20.

Other areas where hybrid probe 20 will be useful in the future is in the identification and characterization of prostate carcinoma with mononoclonal antibody prostascint pancre-atic adenocarcinoma and in parathyroid adenomas. Also, the probe may be used in conjunction with I-125 and palladium radioactive seeds used to treat prostate carcinoma to assist their placement in relation to the carcinoma and prostate gland. Prior diagnostic devices alone have simply been unable to fully characterize these tumors at early stages, which has resulted in increased mortality when these diseases are contracted. Hybrid probes provided in accordance with the present invention would provide early stage diagnosis and would therefore save many lives.

It is envisioned that hybrid probe 20 will be interfaced with a central processing unit (CPU) shown generally at 140 in FIG. 1. CPU 140 will have all the necessary and essential software to integrate the outputs of ultrasound probe 30 and nuclear probe 40 so that accurate and efficient location, characterization and diagnosis of the potentially diseased area 35 can be accomplished. Ultrasound probe 30 may be directly interfaced at 150 to CPU 140. Similarly, nuclear probe 40 may be directly interfaced at 160 to CPU 140. Optionally, counter and power supply 120 may also be interfaced at 170 to CPU 140. More preferably, CPU 140 can be interfaced to a display unit 180. Display unit 180 could be a cathode ray tube (CRT) device or any other device such as a rate meter, recorder, or other personal computer which is adapted to display data gathered by hybrid probe 20.

Figure 2:
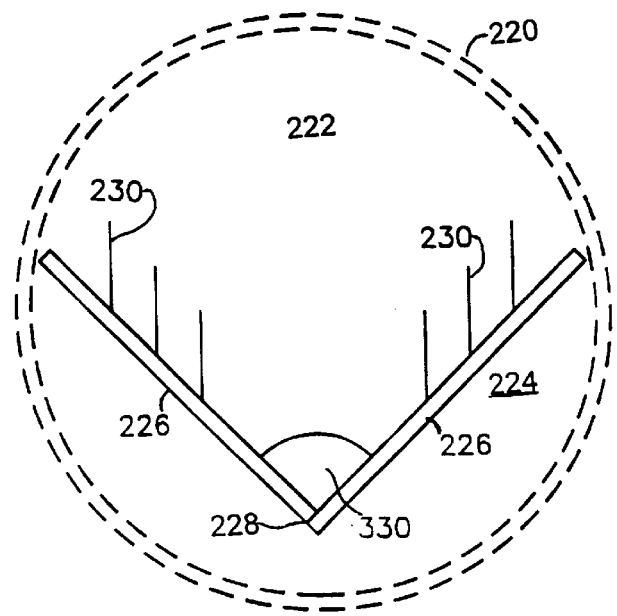
FIG. 2 is a section view of a novel hybrid probe in accordance with the present invention.

Referring to FIGS. 2 through 8, further embodiments of the novel hybrid probe 220 in accordance with the present invention are shown in detail. As shown in FIG. 2, the probe 220 is cylindrical 222 and circular in cross-section. In one embodiment, the probe 220 comprises a nuclear detector 224 comprising substantially perpendicular scintillator plates 226 disposed axially along the length of the probe 220 which meet at an intersection 228 and which includes multiple parallel extending collimators 230. In addition, at the intersection between the scintillator plates 226 the probe has an ultrasonic sensor 330 which extends the length of the scintillator plates 226. The ultrasonic sensor 330 can be a phased array, annular array or linear array scanner, depending upon the desired application. The ultrasonic sensor may comprise a 1.5 D scanner, and may further be electronically steered.

The choice of scanner will depend upon the application required. Electronic array ultrasound scanners are particularly useful for certain types of imaging because they require no moving parts and can be made smaller. Also, linear or even curvilinear array probes offer a larger field of view, which may make anatomic orientation less difficult for the operator. Combinations of array scanners such as linear array with a radial sector phased array scanner or the mounting of separate transducer assemblies on the same ultrasound probe allows visualization of different anatomic planes without exchange of the probe itself during the examination of a patient.

The parallel collimators 230 comprise members having at least one aperture in the radioactive ray detecting direction and made of a radioactive ray attenuating material. Such a material weakens the intensity of radioactive rays and may comprise lead, tungsten, stainless steel lead glass or mercury.

Figure 3:
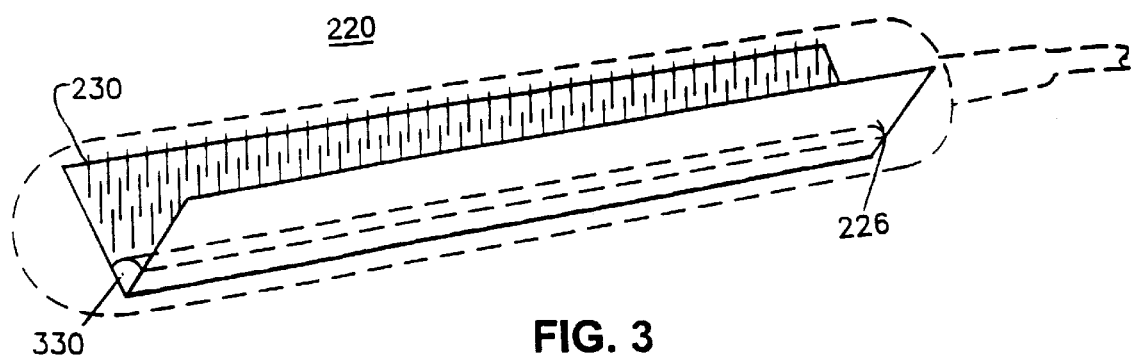
FIG. 3 is a side perspective view of a novel hybrid probe of the present invention.
Figure 4:
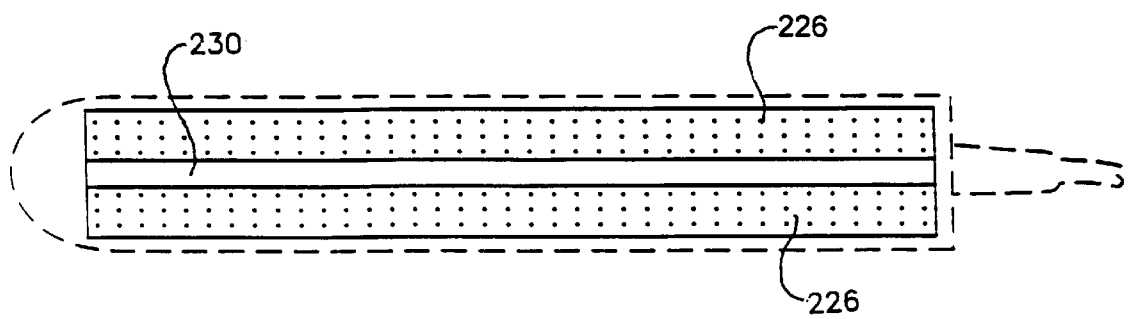
FIG. 4 is a plan view of the hybrid probe of the present invention.

The scintillator surfaces 226 preferably include an aluminum foil surface which functions as a moisture barrier. In the embodiment of FIGS. 2–4, the dual exposed surface areas allow for a greater number of radioactive events to be detected and for the possibility of three dimensional imaging. The physical disposition of the respective ultrasonic 330 and nuclear probes 224 provides for simultaneous ultrasonic and nuclear monitoring with a minimum of interference.

Figure 7:
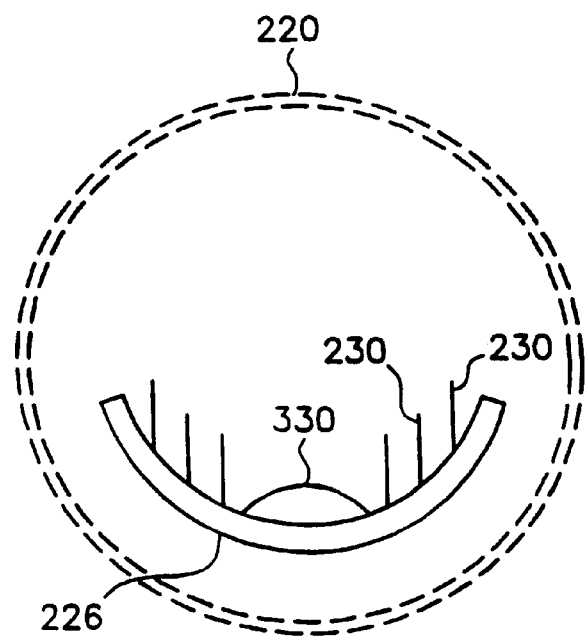
FIG. 7 is an alternative embodiment of a hybrid probe in accordance with the present invention.
Figure 8:
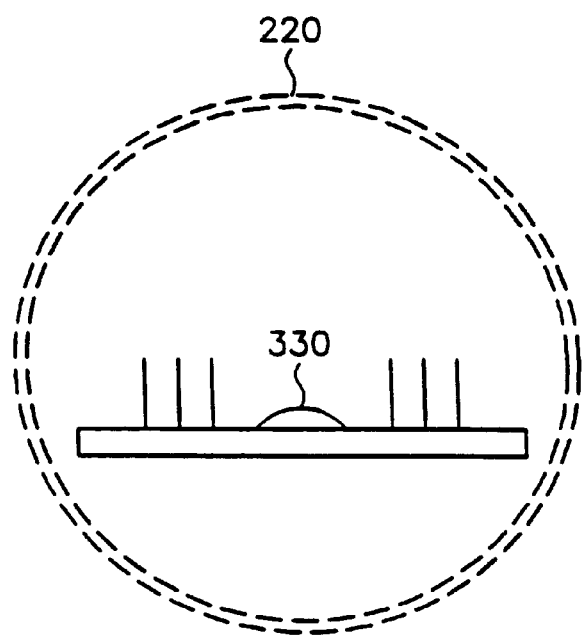
FIG. 8 is still a further alternative embodiment of the hybrid probe of the present invention.

Referring now to FIGS. 7 and 8, further embodiments of the present invention. As shown in FIG. 7, the scintillator plate 226 is curved and includes parallel collimators 230 as in the embodiment of FIGS. 2–4. As with the embodiment in FIG. 7, in FIG. 8, a single flat scintillator plate 226, in association with parallel collimators 230 is used in conjunction with the ultrasonic probe 330.

Figure 5:
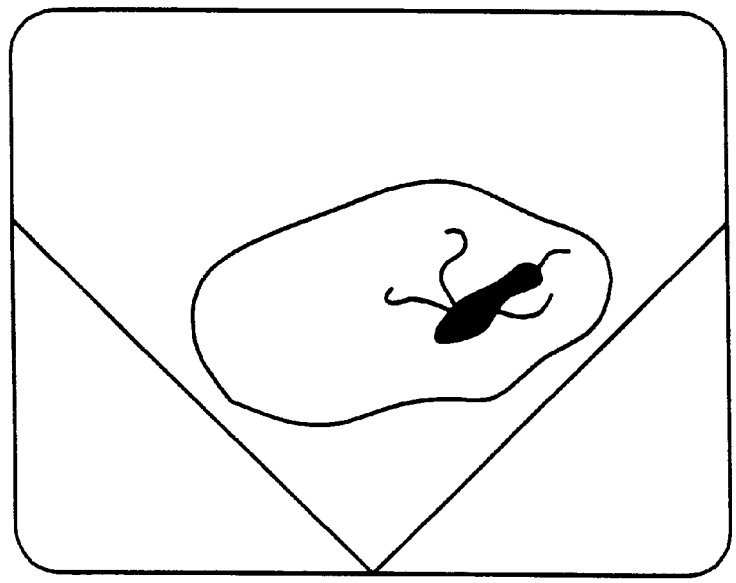
FIG. 5 is a representation of the output of the novel probe of the present invention.
Figure 6:
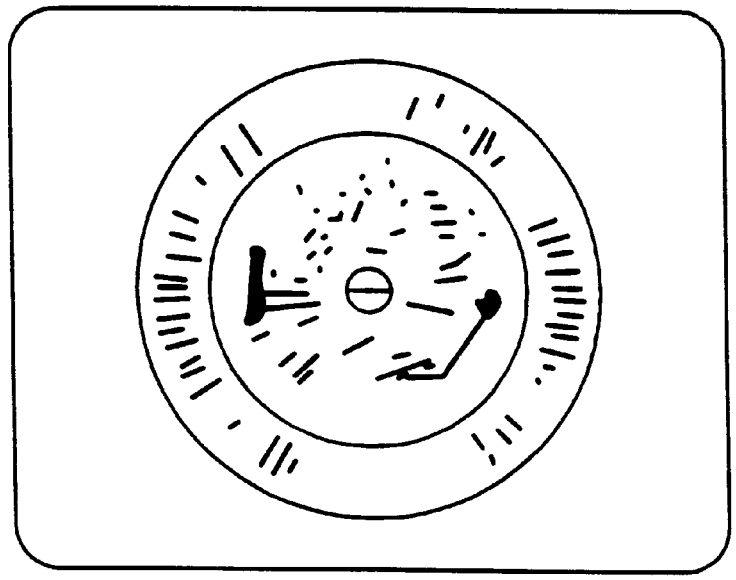
FIG. 6 is a representation of the output of a typical hybrid probe.

The probe of FIGS. 2–4 and 7–8 creates new detection capabilities and diagnostic information gathering by enabling efficient evaluation of diseased tissue in relation to patients anatomy whereby the hybrid probe can both pinpoint the presence of diseased tissue, characterize the diseased tissue and see the relationship to normal anatomic structures. As shown in FIG. 5, X, Y, Z coordinates that coincide with shape, size and relation to vital normal anatomic structures including vascular structures may be shown by the present invention. The X, Y, Z coordinates are obtained by the special design and relationship of the plate-like nuclear detectors and ultrasound probe. Similar coordinates and a 3D perspective cannot be obtained by radioactive ray detecting means arranged in the tip part of an endoscope as described in the Inaba patent. As shown in the FIG. 6, prior art systems by contrast observe the direction of the ultrasonic image device and the detecting direction of the radioactive ray detecting device substantially so as to coincide with each other. Such systems do not provide a single unified view.

The present invention thus provides for the creation of a three dimensional perspective of normal anatomic structures and pathology such as tumors or other disease processes. The result is a fused image where the two modalities are co-existing.

Figure 9A:
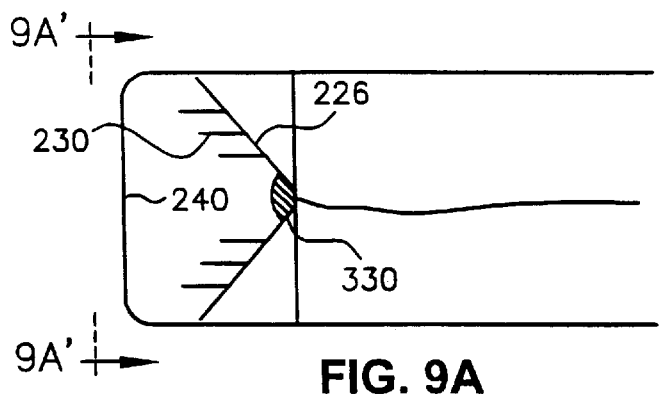
FIGS. 9A–9C are section views of still further embodiments of the present invention in which the scintillators and ultrasonic sensor are situated axially at the tip of the probe.
Figure 9A:
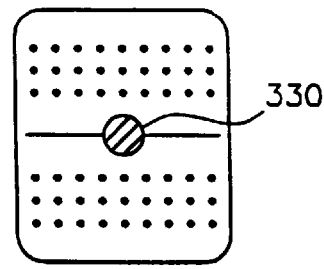
Figure 9B:
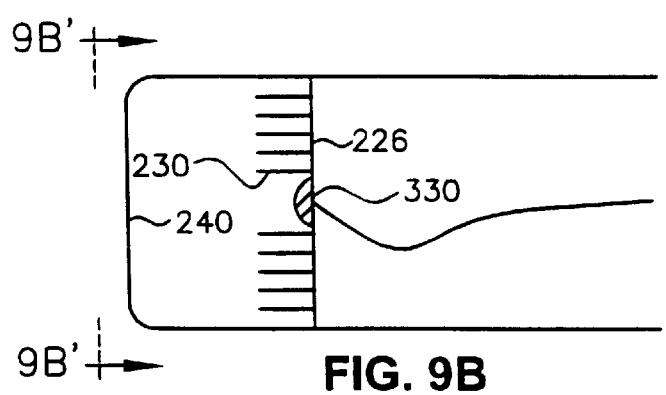
Figure 9B:
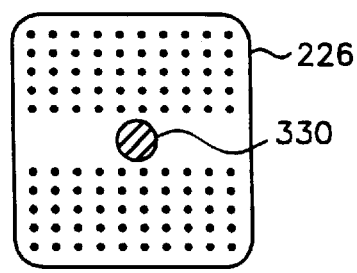
Figure 9C:
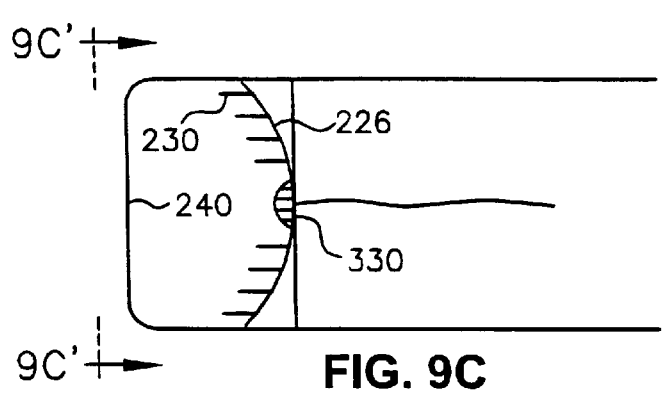
Figure 9C:
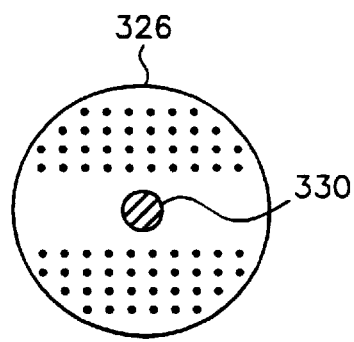

FIGS. 9A–9C illustrate still further embodiments of the invention. In these embodiments, rather than extending longitudinally through the probe length, the respective ultrasonic 330 and nuclear probes 226 extend axially at the tip of the probe 220 which is enclosed within a barrier 340. In FIGS. 9A–9C, the hybrid probe configuration extends axially at the tip of the device. FIG. 9A illustrates an embodiment including perpendicular scintillator plates 226 and parallel collimators 230. FIG. 9B illustrates an embodiment having a flat scintillator plate 226 and parallel collimators 230 and FIG. 9C illustrates an embodiment having a curved scintillator plate. It is to be appreciated that the scintillator plate 226 of this embodiment may be dish shaped 326 as shown in FIG. 9C. In all three embodiments, ultrasonic detector 330 is situated at the center of the scintillator 226 located at the tip of the device behind barrier 340.

The present invention can be applied to a number of applications in the surgical field intraoperatively, whereas endoscopes cannot be used in this fashion. Endoscopes are introduced into a hollow viscous such as the esophagus or colon and have restricted applications. Multiple applications for the present invention extend the utilization of one singular, portable device including numerous cancers such as prostate, breast, ovary and colon.

The design of the probe of the present invention allows for easy integration of acquired images to produce a single, unified image maximizing the abilities of the combined methods. Hybrid probes provided in accordance with the present invention improves the physician's ability to diagnose and characterize potentially harmful diseases. By first locating a diseased area during surgery or otherwise with a nuclear probe, and then interactively fully characterizing the area with an ultrasound probe, diseases which are potentially life-threatening can be detected early and will be more quickly diagnosed. Such results have not heretofore been achieved in the art.

There have thus been described certain preferred embodiments of hybrid ultrasound and nuclear medicine probes provided in accordance with the present invention. While preferred embodiments have been described and disclosed, it will be recognized by those with skill in the art that modifications are within the true spirit and scope of the invention. The appended claims are intended to cover all such modifications.

What is claimed is:

1. A substantially cylindrical probe having an end for locating and characterizing diseases comprising:

a scintillator having parallel collimators for examining a potentially diseased area as a function of electromagnetic radiation emitted from the area;

an ultrasonic sensor situated on said scintillator for examining the potentially diseased area with ultrasonic energy, wherein the scintillator and ultrasonic sensor are adapted to characterize the potentially diseased area interactively; and processing means interfaced to the scintillator and the ultrasonic sensor for analyzing data collected by the scintillator and ultrasonic sensor to characterize the disease in the potentially diseased area.

2. The probe of claim 1, wherein said scintillator comprises two substantially perpendicularly disposed members.

3. The probe of claim 2, wherein said scintillator extends axially out the end of said probe.

4. The probe of claim 1, where said scintillator comprises a curved surface.

5. The probe of claim 4, wherein said scintillator extends axially out the end of said probe.

6. The probe of claim 5, wherein said scintillator is dish shaped.

7. The probe of claim 1, wherein said scintillator comprises a flat surface.

8. The probe of claim 7, wherein said scintillator extends axially out the end of said probe.

9. The probe recited in claim 1 further comprising a display unit interfaced with the processing means for displaying data which has been analyzed by the processing means.

10. A novel hybrid probe comprising:

a cylindrical outer casing having an axial length and surrounding a nuclear probe, said nuclear probe comprising a scintillator extending axially the length of the casing, said scintillator having a plurality of parallel collimators extending therefrom; and an ultrasonic probe affixed within the casing on said scintillator and extending the length of the scintillator.

11. The novel hybrid probe of claim 10, wherein said scintillator comprises two scintillator plates intersecting substantially perpendicularly, and said ultrasonic probe is situated at the intersection of the scintillator plates and extends their lengths.

12. The novel hybrid probe of claim 10, wherein said scintillator is curved.

13. The novel hybrid probe of claim 10 wherein said scintillator is flat.

* * * * *